United States Patent [19]
Sugano et al.

[11] Patent Number: 6,124,501
[45] Date of Patent: Sep. 26, 2000

[54] PROCESS FOR PREPARING LACTAMIDE

[75] Inventors: Yuichi Sugano; Takafumi Abe; Rieko Nakano, all of Niigata-ken, Japan

[73] Assignee: Mitsubishi Gas Chemical Company, Inc., Tokyo, Japan

[21] Appl. No.: 09/261,858

[22] Filed: Mar. 3, 1999

[30] Foreign Application Priority Data

Mar. 24, 1998 [JP] Japan ................................. 10-075788

[51] Int. Cl.$^7$ .................................................. C07C 231/06
[52] U.S. Cl. ........................ 564/126; 564/125; 564/130; 564/201
[58] Field of Search ..................... 564/126, 201, 564/125, 130

[56] References Cited

U.S. PATENT DOCUMENTS 5,087,750  2/1992  Uda et al. ................................ 564/126

FOREIGN PATENT DOCUMENTS 0 773 212  5/1997  European Pat. Off. .

OTHER PUBLICATIONS

Patent Abstracts of Japan, vol. 6, No. 006, Jul. 31, 1995, Abstract of JP 07–061961 A, Mar. 7, 1995.

*Primary Examiner*—Shailendra Kumar
*Attorney, Agent, or Firm*—Frishauf, Holtz, Goodman, Langer & Chick, P.C.

[57] ABSTRACT

A process for preparing lactamide with a high conversion and a high selectivity without the deterioration of a catalytic activity in a short time, which comprises subjecting lactonitrile to a hydrating reaction in the presence of (A) a catalyst including an oxide of manganese as a main component, (B) an oxidizing agent and (C) hydrogen cyanide or hydrogen cyanide and a compound represented by the formula

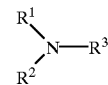

wherein $R^1$, $R^2$ and $R^3$ are each a hydrogen atom, a $C_1$ to $C_8$ alkyl group, a $C_1$ to $C_8$ hyroxyalkyl group, a $C_1$ to $C_8$ aminoalkyl group or a $C_1$ to $C_8$ halogenoalkyl group.

19 Claims, No Drawings

PROCESS FOR PREPARING LACTAMIDE

BACKGROUND OF THE INVENTION

(1) Field of the Invention

The present invention relates to an improvement of a process for preparing lactamide. More specifically, the present invention relates to an industrially advantageous process for efficiently preparing lactamide, which can be used as a raw material for various kinds of organic products such as lactates and lactic acid which are useful as materials for organic synthesis and solvents, by a hydrating reaction of lactonitrile.

(2) Description of the Related Art

It is known that lactamide can be converted into a lactate by an amide-ester exchange reaction with a formate or by an alcoholysis, and this lactate can then be subjected to a hydrolysis treatment to thereby prepare lactic acid. Needless to say, the above-mentioned lactate and lactic acid are useful as materials for organic synthesis and solvents, and particularly, lactic acid is useful as a mildewproofing agent and a raw material of a biologically degradable polymer. Furthermore, the lactate can be utilized as a raw material for manufacturing an acrylate with the aid of a dehydrating reaction, and so it is industrially important and applicable to many uses.

As understood from the above, lactamide is an extremely important compound as a raw material for the lactates, lactic acid and various organic products.

Now, it has been suggested to use b type manganese dioxide as a catalyst in a hydrating reaction of acetone cyanhydrin (the specification of U.S. Pat. No. 4018829). As techniques for preparing manganese dioxide for hydrating acetone cyanhydrin, there are disclosed a method comprising the step of introducing zinc thereinto, a method comprising the step of reducing potassium permanganate with hydrochloric acid (Japanese Patent Application Laid-Open Nos. 57534/1988 and 57535/1988), and a method comprising the step of reducing a permanganate with hydrazine, a hydroxycarboxylic acid or its salt (Japanese Patent Application Laid-Open No. 269666/1994).

On the other hand, it has been suggested that manganese dioxide is used as a catalyst in a hydrating reaction of lactonitrile belonging to a cyanhydrin like acetone cyanhydrin mentioned above (specifications of Japanese Patent Publication No. 47822/1986 and U.S. Pat. No. 5,175,366). In addition, there is disclosed a hydrating reaction of lactonitrile in the presence of a catalyst comprising manganese dioxide prepared by a method which comprises reducing a permanganate with a polyhydric alcohol, or a method which comprises reducing it with a polyvalent carboxylic acid or its salt (Japanese Patent Application Laid-Open Nos. 19637/1997 and 24275/1997).

However, when manganese dioxide prepared by either of the above-mentioned method is directly used as it is as the catalyst for the hydrating reaction of lactonitrile, there is a problem that its catalytic activity rapidly deteriorates in a short period of time, and for this reason, the aforesaid techniques have not been put to practical use so far.

SUMMARY OF THE INVENTION

The present invention has been developed under such circumstances, and its object is to provide an industrially advantageous process for efficiently preparing lactamide by a hydrating reaction of lactonitrile with a high conversion and a high selectivity without the deterioration of a catalytic activity in a short time.

The present inventors have intensively researched with the intention of achieving the above-mentioned object, and as a result, it has been found that when lactamide is prepared by the hydrating reaction of lactonitrile in the presence of a catalyst including an oxide of manganese as a main component, the rapid deterioration of the catalytic activity can be inhibited by allowing an oxidizing agent to coexist in the hydrating reaction. It has also been found that when the reaction is carried out in the simultaneous presence of the oxidizing agent and a nitrogen-containing compound, the activity deterioration is more inhibited and a conversion is more improved as compared with a case where the oxidizing agent alone is present. It has further been found that the reaction is carried out in the simultaneous presence of the oxidizing agent and hydrogen cyanide, the activity deterioration is more inhibited and the selectivity of lactamide is more improved as compared with the case where the oxidizing agent alone is present. Moreover, it has further been found that the reaction is carried out in the simultaneous presence of the oxidizing agent, the nitrogen-containing compound and hydrogen cyanide, the respective effects of the nitrogen-containing compound and hydrogen cyanide can synergistically be obtained. In consequence, the present invention has been completed.

That is to say, (1) the first aspect of the present invention is directed to a process for preparing lactamide which comprises the step of subjecting lactonitrile to a hydrating reaction in the presence of (A) a catalyst including an oxide of manganese as a main component and (B) an oxidizing agent (hereinafter referred to as "the first invention").

(2) The second aspect of the present invention is directed to a process for preparing lactamide which comprises the step of subjecting lactonitrile to a hydrating reaction in the presence of (A) a catalyst including an oxide of manganese as a main component, (B) an oxidizing agent and (C) at least one selected from the group consisting of hydrogen cyanide and compounds represented by the general formula (I)

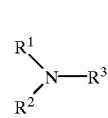

(I)

wherein $R^1$, $R^2$ and $R^3$ are each a hydrogen atom, an alkyl group having 1 to 8 carbon atoms, a hydroxyalkyl group having 1 to 8 carbon atoms, an aminoalkyl group having 1 to 8 carbon atoms or a halogenoalkyl group having 1 to 8 carbon atoms, and they may be the same or different (hereinafter referred to as "the second invention").

PREFERRED EMBODIMENTS OF THE INVENTION

The present invention includes the first invention in which a hydrating reaction of lactonitrile is carried out in the presence of (A) a catalyst and (B) an oxidizing agent, and the second invention in which the hydrating reaction of lactonitrile is carried out in the presence of (A) a catalyst, (B) an oxidizing agent and (C) at least one selected from the group consisting of nitrogen-including compounds and hydrogen cyanide.

In the present invention (the first and second inventions), no particular restriction is put on the origin of lactonitrile which can be used as a raw material, and lactonitrile obtained in any manner is acceptable. For example, lactonitrile can easily be prepared by reacting acetaldehyde with hydrogen cyanide in the presence of a basic catalyst.

The catalyst which is the component (A) in the first and second inventions includes an oxide of manganese as a main component. Usually, as such a catalyst, there is preferably used a catalyst including manganese dioxide as the main component. Manganese dioxide is an oxide of manganese present as between $MnO_{1.7}$ and $MnO_2$, and with regard to their crystal structures, $\alpha$, $\beta$, $\gamma$, $\delta$, $\epsilon$ and the like are known. Since a transition between phases and a change of crystallinity occur, the extremely complex and various structures are present. Manganese dioxide also exists in nature, but in the case that it is used as the catalyst, manganese dioxide obtained by oxidizing a divalent manganese compound, and manganese dioxide obtained by reducing a heptavalent manganese compound are suitable.

Needless to say, manganese dioxide obtained by the reaction of the divalent manganese compound with the heptavalent manganese compound is also suitable as the catalyst.

No particular restriction is put on a method for preparing manganese dioxide by oxidizing the divalent manganese compound and a method for preparing manganese dioxide by reducing the heptavalent manganese compound, and conventional known methods can be used.

For example, as the method for preparing manganese dioxide by oxidizing the divalent manganese compound, there can be used a method which comprises electrolytically oxidizing an aqueous manganese sulfate solution. On the other hand, as the method for preparing manganese dioxide by reducing the heptavalent manganese compound, there can be used a method which comprises reducing a permanganic acid compound at a temperature of about 20 to 100° C. in a neutral or an alkali range ["Zeit. Anorg. Allg. Chem.", Vol. 309, p. 1–32 and p. 121–150 (1961)], a method which comprises reducing a permanganate with a hydrohalogenic acid (Japanese Patent Application Laid-Open No. 57535/1988), a method which comprises reducing a permanganate with a polyvalent carboxylic acid or a polyhydric alcohol (Japanese Patent Application Laid-Open No. 24275/1997 and 19637/1997), and a method which comprises reducing a permanganate with hydrazine, a hydroxycarboxylic acid or its salt (Japanese Patent Application Laid-Open No. 269666/1994).

Furthermore, as the method for preparing manganese dioxide by the use of the divalent manganese compound and the heptavalent manganese compound, there can be used a method which comprises mixing an aqueous potassium permanganate solution and an aqueous manganese sulfate solution ["J. Chem. Soc.", p. 2189 (1953)].

As the catalyst including the oxide of manganese as the main component which can be used in the process of the present invention, manganese dioxide prepared by any of the above-mentioned various methods can be used, but particularly, a modified manganese dioxide containing an alkaline metallic element is preferable. An advantageous method for preparing this kind of catalyst comprises simultaneously using the divalent manganese compound and the heptavalent manganese compound in that the type of crystals, the size of a specific surface area, and the kind and the amount of alkali metal can be controlled.

To the manganese dioxide catalyst or the modified manganese dioxide containing the alkaline metallic element, other elements, for example, elements in the groups 2, 3, 4, 5, 6, 8, 9, 10, 11, 12, 13, 14 and 15 of the periodic table can be added, as needed. In particular, it is preferable to add at least one metallic element selected from the group consisting of alkaline earth metals, Sc, Zr, V, Nb, Ta, Cr, Mo, W, Zn, Ga, In, Ge, Sn and Pb. Adding these metallic elements to manganese dioxide can be accomplished by any technique of impregnation, adsorption, kneading, co-precipitation and the like, but the co-precipitation method is particularly suitable.

The modified manganese dioxide containing the metallic element can be prepared in either of an acidic atmosphere and a basic atmosphere, but the preparation in the acidic atmosphere is preferable. In the case that the preparation is made in the basic atmosphere, the modified manganese dioxide is suitably washed with an acidic solution prior to its use as the catalyst.

The divalent manganese compound which can be used for the above-mentioned preparation of the catalyst is preferably in the form of a water-soluble salt, particularly preferably a sulfate. On the other hand, the heptavalent manganese compound is particularly preferably a water-soluble potassium permanganate or sodium permanganate, and this compound can also be used as an alkali metal source. The source of the alkaline earth metal, Sc, Zr, V, Nb, Ta, Cr, Mo, W, Zn, Ga, In, Ge, Sn or Pb which can be added to manganese dioxide is preferably in the form of a water-soluble salt, particularly preferably a sulfate.

In the thus obtained modified manganese dioxide, a molar ratio of the alkali metal and another metal to manganese is preferably in the range of 0.005 to 0.5 and 0.001 to 0.3, respectively, more preferably 0.05 to 0.3 and 0.005 to 0.1, respectively.

In the present invention, the thus prepared catalyst can be supported on a metallic oxide carrier such as alumina, silica, zirconia or titania prior to its use. A molded article of the catalyst can be used as a fixed bed catalyst, or powder, granules or minute spheres are used as a slurry catalyst in the hydrating reaction of lactonitrile in a batch system or a flow system reactor.

Next, examples of the oxidizing agent which is the component (B) in the first and second inventions include oxygens such as oxygen and ozone, peroxides such as hydrogen peroxide, sodium peroxide, magnesium peroxide, benzoyl peroxide and diacetyl peroxide, peracids and their salts such as performic acid, peracetic acid and ammonium persulfonate, and oxyacids and their salts such as periodic acid, perchloric acid, sodium periodate, iodic acid, bromic acid, potassium chlorate and sodium hypochlorite. Above all, the oxygens are preferable, and oxygen is particularly prefer- able. These oxidizing agents may be used singly or in the form of a mixture of two or more thereof.

In the present invention, the above-mentioned oxidizing agent is usually fed by being dissolved or dispersed in a raw material solution, and its amount to be added is preferably selected in the range of 0.001 to 0.15 mol, more preferably 0.005 to 0.05 mol per mol of lactonitrile which is the raw material. If the amount of the oxidizing agent is less than 0.001 mol, the effect of controlling the rapid deterioration of a catalytic activity would not sufficiently be exerted, and if it is more than 0.15 mol, the corresponding improvement of the effect would not be observed.

In the case that oxygen is used as the oxidizing agent, pure oxygen may be used, but prior to its use, it is usually diluted with an inert gas such as nitrogen. Needless to say, air may directly be used as it is, or prior to its use, it may be mixed with oxygen or the inert gas to adjust the concentration of oxygen. The oxygen concentration of the oxygen-containing gas is optional, but it is usually selected in the range of 2 to 50% by volume. When the oxygen gas is used, it is particularly preferable to use the so-called trickle bed type reactor in which the fixed bed is filled with the catalyst and a reaction solution flows between a solid phase and a gaseous phase, whereby the good dispersion of the gas in the reaction solution and the good contact of the reaction solution with the catalyst can be achieved. The flow of the reaction solution and the gas in the reactor may be either of a counter flow and a parallel flow.

In the second invention, the nitrogen-including compound or hydrogen cyanide is used as the component (C) together with the catalyst as the component (A) and the oxidizing agent as the component (B) to carry out the hydrating reaction of lactonitrile.

As the nitrogen-including compound, there is used a compound having a structure represented by the general formula (I):

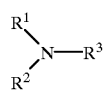

In the above-mentioned general formula (I), $R^1$, $R^2$ and $R^3$ are each a hydrogen atom, an alkyl group having 1 to 8 carbon atoms, a hydroxyalkyl group having 1 to 8 carbon atoms, an aminoalkyl group having 1 to 8 carbon atoms or a halogenoalkyl group having 1 to 8 carbon atoms, and they may be the same or different. Here, the alkyl group having 1 to 8 carbon atoms may be any of straight-chain, branched or cyclic, and typical examples of the alkyl group include a methyl group, an ethyl group, an n-propyl group, an isopropyl group, an n-butyl group, an isobutyl group, a sec-butyl group, a tert-butyl group, various pentyl groups, various hexyl groups, various heptyl groups, various octyl groups and cycloalkyl groups having 3 to 8 carbon atoms such as a cyclopentyl group, a cyclohexyl group and a cyclooctyl group.

The hydroxyalkyl group having 1 to 8 carbon atoms is a group in which one or more hydrogen atoms of the above-mentioned alkyl group are substituted by one or more hydroxyl groups, and the aminoalkyl group having 1 to 8 carbon atoms is a group in which one or more hydrogen atoms of the above-mentioned alkyl group are substituted by one or more amino groups. Furthermore, the halogenoalkyl group having 1 to 8 carbon atoms is a group in which one or more hydrogen atoms of the above-mentioned alkyl group are substituted by one or more of halogen atoms such as fluorine atoms, chlorine atoms, bromine atoms and iodine atoms.

Examples of the nitrogen-including compound represented by the general formula (I) include ammonia, monoethylamine, diethylamine, triethylamine, monomethylamine, dimethylamine, trimethylamine, monopropylamine, dipropylamine, tripropylamine, monoisopropylamine, diisopropylamine, triisopropylamine, monoethanolamine, diethnolamine, triethanolamine, ethylenediamine and diethylenetriamine.

In the second invention, as the component (C), there may be used one or more of the above-mentioned nitrogen-containing compounds, hydrogen cyanide alone, or a combination of one or more of the nitrogen-containing compounds and hydrogen cyanide.

In the second invention, when the oxidizing agent and the nitrogen-containing compound coexist, the activity deterioration can be more inhibited and the conversion can be more improved as compared with a case where the oxidizing agent alone is present. Furthermore, when the oxidizing agent and hydrogen cyanide coexist, the activity deterioration can be more inhibited and the selectivity of lactamide can be more improved as compared with the case where the oxidizing agent alone is present.

Such effects of the nitrogen-containing compound and hydrogen cyanide, which can be obtained in addition to the effect of the oxidizing agent, can synergistically be exerted in the case that both the nitrogen-containing compound and hydrogen cyanide are added to the oxidizing agent, whereby the conversion, the selectivity and the longevity of the catalyst can be more improved. This fact will be apparent from the undermentioned examples.

In view of the above-mentioned effects, the amount of the nitrogen-containing compound to be added is usually in the range of 0.0001 to 5% by weight, preferably 0.0005 to 3% by weight based on the weight of lactonitrile which is the raw material. Similarly in view of the above-mentioned effects, the amount of hydrogen cyanide to be added is usually 0.001 to 2% by weight based on the weight of lactonitrile which is the raw material.

In the first invention, lactonitrile is subjected to the hydrating reaction in the presence of the catalyst as the component (A) and the oxidizing agent as the component (B), and in the second invention, lactonitrile is subjected to the hydrating reaction in the presence of the catalyst as the component (A), the oxidizing agent as the component (B) and the nitrogen-containing compound and/or hydrogen cyanide as the component (C). The weight ratio of lactonitrile to water in this hydrating reaction of lactonitrile is usually in the range of 5:95 to 80:20, preferably 20:80 to 60:40 from the viewpoint of reactivity. A reaction system which can be employed in the present invention may be any of a batch system, a semi-batch system and a continuous system, but a continuous reaction system in which a flow type reactor including a fixed bed catalyst is used is preferable.

A temperature of the hydrating reaction is usually in the range of 0 to 120° C. If this temperature is less than 0C, a reaction rate is so slow as to be impractical, and if it is more than 120° C., lactonitrile tends to decompose, whereby by-products inconveniently increase. In consideration of the reaction rate and the amounts of the by-products, the reaction temperature is preferably in the range of 10 to 90° C. No particular restriction is put on a reaction pressure, but the reaction can usually be carried out under a pressure in the vicinity of atmospheric pressure.

According to the process of the present invention, lactamide can efficiently be prepared with the high conversion and selectivity by subjecting lactonitrile to the hydrating reaction, while the high catalytic activity is maintained for a long period of time. Therefore, the process for preparing lactamide of the present invention is industrially extremely advantageous.

Next, the present invention will be described in more detail in accordance with examples, but the scope of the present invention should not be limited at all by these examples.

COMPARATIVE EXAMPLE 1

Preparation of a catalyst: A solution obtained by dissolving 0.316 mol of manganese sulfate monohydrate and 0.0137 mol of tin sulfate in 200 ml of water and then mixing the aqueous solution with 0.968 mol of concentrated sulfuric acid was promptly poured at 70° C. with stirring into another solution obtained by dissolving 0.398 mol of potassium permanganate in 200 ml of water. After aging at 90° C. for 2 hours with continuous stirring, the resultant precipitate was collected by filtration, and then washed 5 times with 2000 ml of water. The resultant cake was dried at 110° C. overnight to obtain 64 g of a modified manganese dioxide. According to measurement, the ratio of the metallic components in the modified manganese dioxide was tin/potassium/manganese=0.02/0.08/1 (an atomic ratio).

Reaction: The thus obtained modified manganese dioxide was uniformly ground to a particle size of 10 to 20 mesh, and 4.5 cc of the resultant particles was then filled into a glass reactor having an internal diameter of 10 mm and equipped with a jacket, through which warm water at 40° C. was allowed to flow. A raw material solution obtained by mixing 35.000 parts by weight of lactonitrile with 65.000 parts by weight of water was fed to a reactor from its upper portion at a flow rate of 4.3 g/hr. The solution coming from the reactor was refed to the reactor through its inlet at 43 g/hr (a circulation ratio=10) by a circulating pump. The reaction solution overflowed from a liquid tank under the reactor was analyzed after 24 hours and 10 days from the start of reaction by a high-performance liquid chromatography to inspect its composition. As a result, the conversions of lactonitrile were 80.2% and 61.0%, respectively. In addition, the selectivities (based on lactonitrile) of lactamide after 24 hours and 10 days were 94.6% and 95.0%, respectively.

COMPARATIVE EXAMPLE 2

Reaction was carried out by the same procedure as in Comparative Example 1 except that nitrogen was fed to a reactor from its upper portion at a flow rate of 35 ml/hr. After 24 hours and 10 days from the start of the reaction, analysis was made. As a result, the conversions of lactoni- trile were 79.7% and 58.3%, respectively. In addition, the selectivities (based on lactonitrile) of lactamide after 24 hours and 10 days were 94.8% and 94.5%, respectively.

EXAMPLE 1

Reaction was carried out by the same procedure as in Comparative Example 1 except that air was fed to a reactor from its upper portion at a flow rate of 35 ml/hr. After 24 hours and 10 days from the start of the reaction, analysis was made. As a result, the conversions of lactonitrile were 80.0% and 67.3%, respectively. In addition, the selectivi- ties (based on lactonitrile) of lactamide after 24 hours and 10 days were 95.0% and 95.0%, respectively.

EXAMPLE 2

Reaction was carried out by the same procedure as in Comparative Example 1 except that air was fed to a reactor from its upper portion at a flow rate of 35 ml/hr and a raw material solution obtained by mixing 35.000 parts by weight of lactonitrile, 64.490 parts by weight of water and 0.510 part by weight of trimethylamine was used. After 24 hours and 10 days from the start of the reaction, analysis was made. As a result, the conversions of lactonitrile were 85.1% and 84.3%, respectively. In addition, the selectivi- ties (based on lactonitrile) of lactamide after 24 hours and 10 days were 95.2% and 95.1%, respectively.

EXAMPLE 3

Reaction was carried out by the same procedure as in Comparative Example 1 except that air was fed to a reactor from its upper portion at a flow rate of 35 ml/hr and a raw material solution obtained by mixing 35.000 parts by weight of lactonitrile, 64.330 parts by weight of water, 0.510 part by weight of trimethylamine and 0.160 part by weight of hydrogen cyanide was used. After 24 hours and 10 days from the start of the reaction, analysis was made. As a result, the conversions of lactonitrile were 84.8% and 84.1%, respectively. In addition, the selectivities (based on lactonitrile) of lactamide after 24 hours and 10 days were 97.0% and 97.2%, respectively.

EXAMPLE 4

Reaction was carried out by the same procedure as in Comparative Example 1 except that a raw material solution obtained by mixing 0.100 part by weight of hydrogen peroxide, 35.000 parts by weight of lactonitrile and 64.900 parts by weight of water was used. After 24 hours and 10 days from the start of the reaction, analysis was made. As a result, the conversions of lactonitrile were 80.5% and 69.1%, respectively. In addition, the selectivities (based on lactonitrile) of lactamide after 24 hours and 10 days were 94.8% and 95.0%, respectively.

EXAMPLE 5

Reaction was carried out by the same procedure as in Comparative Example 1 except that a raw material solution obtained by mixing 0.175 part by weight of hydrogen cyanide, 35.000 parts by weight of lactonitrile and 64.825 parts by weight of water was used and air was fed to a reactor from its upper portion at a flow rate of 35 ml/hr. After 24 hours and 10 days from the start of the reaction, analysis was made. As a result, the conversions of lactonitrile were 80.3% and 73.1%, respectively. In addition, the selectivities (based on lactonitrile) of lactamide after 24 hours and 10 days were 97.0% and 97.5%, respectively.

COMPARATIVE EXAMPLE 3

Preparation of a catalyst: A solution obtained by dissolv- ing 0.316 mol of manganese sulfate monohydrate in 200 ml of water and then mixing the aqueous solution with 0.968 mol of concentrated sulfuric acid was promptly poured at 70° C. with stirring into another solution obtained by dis- solving 0.398 mol of potassium permanganate in 200 ml of water. After aging at 90° C. for 2 hours with continuous stirring, the resultant precipitate was collected by filtration, and then washed 5 times with 2000 ml of water. The resultant cake was dried at 110° C. overnight to obtain 64 g of a modified manganese dioxide. According to measurement, the ratio of the metallic components in the modified manganese dioxide was potassium/manganese= 0.09/1 (an atomic ratio).

Reaction: The thus obtained modified manganese dioxide was uniformly ground to a particle size of 10 to 20 mesh, and 4.5 cc of the resultant particles was then filled into a glass reactor having an internal diameter of 10 mm and equipped with a jacket, through which warm water at 40° C. was allowed to flow. A raw material solution obtained by mixing 35.000 parts by weight of lactonitrile with 65.000 parts by weight of water was fed to the reactor from its upper portion at a flow rate of 4.3 g/hr. The solution coming from the reactor was refed to the reactor through its inlet at 43 g/hr (a circulation ratio =10) by a circulating pump. The reaction solution overflowed from a liquid tank under the reactor was analyzed after 24 hours and 10 days from the start of reaction by a high-performance liquid chromatography to inspect its composition. As a result, the conversions of lactonitrile were 78.3% and 56.5%, respectively. In addition, the selectivities (based on lactonitrile) of lactamide after 24 hours and 10 days were 95.0% and 95.3%, respectively.

EXAMPLE 6

Reaction was carried out by the same procedure as in Comparative Example 3 except that air was fed to a reactor from its upper portion at a flow rate of 35 ml/hr. After 24 hours and 10 days from the start of the reaction, analysis was made. As a result, the conversions of lactonitrile were 79.2% and 68.6%, respectively. In addition, the selectivities (based on lactonitrile) of lactamide after 24 hours and 10 days were 95.0% and 94.9%, respectively.

EXAMPLE 7

Reaction was carried out by the same procedure as in Comparative Example 3 except that air was fed to a reactor from its upper portion at a flow rate of 35 ml/hr and a raw material solution obtained by mixing 35.000 parts by weight of lactonitrile, 64.260 parts by weight of water and 0.74 part by weight of diethylamine was used. After 24 hours and 10 days from the start of the reaction, analysis was made. As a result, the conversions of lactonitrile were 82.3% and 81.5%, respectively. In addition, the selectivities (based on lactonitrile) of lactamide after 24 hours and 10 days were 95.0% and 95.1%, respectively.

EXAMPLE 8

Reaction was carried out by the same procedure as in Comparative Example 3 except that air was fed to a reactor from its upper portion at a flow rate of 35 ml/hr and a raw material solution obtained by mixing 35.000 parts by weight of lactonitrile, 64.110 parts by weight of water, 0.74 part by weight of diethylamine and 0.15 part by weight of hydrogen cyanide was used. After 24 hours and 10 days from the start of the reaction, analysis was made. As a result, the conversions of lactonitrile were 82.4% and 81.5%, respectively. In addition, the selectivities (based on lactonitrile) of lactamide after 24 hours and 10 days were 97.1% and 97.3%, respectively.

COMPARATIVE EXAMPLE 4

Preparation of a catalyst: The preparation was carried out in the following manner, referring to Japanese Patent Application Laid-Open No. 24275/1997. 0.06 mol of concentrated sulfuric acid was slowly added to an aqueous potassium permanganate solution obtained by dissolving 0.625 mol of potassium permanganate in 110 ml of water, followed by heating to 30° C. To the resultant solution, an aqueous oxalic acid solution obtained by dissolving 0.125 mol of oxalic acid in 130 ml of water was added with stirring while a reaction temperature was adjusted in the range of 30 to 35° C. After completion of the addition, the solution was heated, and then allowed to age at 90° C. for 3 hours with stirring. The resultant slurry was filtered, and the precipitated cake was washed with pure water until a sulfate group was not detected any more, dried at 110° C., and then ground, thereby obtaining a black manganese dioxide catalyst.

Reaction: The thus obtained manganese dioxide was uniformly ground to a particle size of 10 to 20 mesh, and 17 cc of the resultant particles was then filled into a glass reactor having an internal diameter of 10 mm and equipped with a jacket, through which warm water at 40° C. was allowed to flow. A raw material solution obtained by mixing 35.000 parts by weight of lactonitrile with 65.000 parts by weight of water was fed to the reactor at a flow rate of 4.3 g/hr. The solution coming from the reactor was refed to the reactor through its inlet at 43 g/hr (a circulation ratio=10) by a circulating pump. The reaction solution overflowed from a liquid tank under the reactor was analyzed after 24 hours and 10 days from the start of reaction by a high- performance liquid chromatography to inspect its composition. As a result, the conversions of lactonitrile were 79.6% and 57.0%, respectively. In addition, the selectivities (based on lactonitrile) of lactamide after 24 hours and 10 days were 95.2% and 95.4%, respectively.

EXAMPLE 9

Reaction was carried out by the same procedure as in Comparative Example 4 except that air was fed to a reactor from its upper portion at a flow rate of 35 ml/hr. After 24 hours and 10 days from the start of the reaction, analysis was made. As a result, the conversions of lactonitrile were 80.2% and 67.5%, respectively. In addition, the selectivities (based on lactonitrile) of lactamide after 24 hours and 10 days were 95.0% and 95.4%, respectively.

What is claimed is:

1. A process for preparing lactamide which comprises subjecting lactonitrile to a hydrating reaction in the presence of component (A) a catalyst including an oxide of manganese as a main component, component (B) an oxidizing agent and component (C) comprising hydrogen cyanide.

2. The process according to claim 1 wherein said component (C) further comprises at least one compound selected from the group consisting of compounds represented by the formula (I)

(I)

wherein $R^1$, $R^2$ and $R^3$ are the same or different and are each a hydrogen atom, an alkyl group having 1 to 8 carbon atoms, a hydroxyalkyl group having 1 to 8 carbon atoms, an aminoalkyl group having 1 to 8 carbon atoms or a halogenoalkyl group having 1 to 8 carbon atoms.

3. The process according to claim 2 wherein the catalyst (A) including the oxide of manganese as the main component is a catalyst including an oxide of manganese modified with an alkaline metallic element as the main component.

4. The process according to claim 3 wherein the catalyst including an oxide of manganese modified with an alkaline metallic element as the main component is a catalyst including a modified manganese dioxide containing an alkaline metallic element as the main component.

5. The process according to claim 4 wherein the modified manganese dioxide containing an alkaline metallic element is obtained by oxidizing a divalent manganese compound.

6. The process according to claim 4 wherein the modified manganese dioxide containing an alkaline metallic element is obtained by reducing a heptavalent manganese compound.

7. The process according to claim 2 wherein the oxidizing agent (B) is at least one agent selected from the group consisting of oxygens, peroxides, peracids, salts of the peracids, oxyacids and salts of the oxyacids.

8. The process according to claim 2 wherein the temperature of the hydrating reaction is in the range of 0 to 120° C.

9. The process according to claim 3 wherein the catalyst further includes another metal selected from the group consisting of an alkaline earth metal, Sc, Zr, V, Nb, Ta, Cr, Mo, W, Zn, Ga, In, Ge, Sn and Pb.

10. The process according to claim 9 wherein a molar ratio of the alkali metal to manganese is 0.005 to 0.5, and a molar ratio of the another metal to manganese 0.001 to 0.3.

11. The process according to claim 9 wherein a molar ratio of the alkali metal to manganese is 0.05 to 0.3, and a molar ratio of the another metal to manganese 0.005 to 0.1.

12. The process according to claim 7 wherein the oxidizing agent is selected from the group consisting of oxygen, ozone, hydrogen peroxide, sodium peroxide, magnesium peroxide, benzoyl peroxide, diacetyl peroxide, performic acid, peracetic acid, ammonium persulfonate, periodic acid, perchloric acid, sodium periodate, iodic acid, bromic acid, potassium chlorate and sodium hydrochlorite.

13. The process according to claim 12 wherein the oxidizing agent is in an amount of 0.001 to 0.15 mol per mol of lactonitrile.

14. The process according to claim 12 wherein the oxidizing agent is in an amount of 0.005 to 0.05 mol per mol of lactonitrile.

15. The process according to claim 2 wherein the compound of formula (I) is selected from the group consisting of ammonia, monoethylamine, diethylamine, triethylamine, monomethylamine, dimethylamine, trimethylamine, monopropylamine, dipropylamine, tripropylamine, monoisopropylamine, diisopropylamine, triisopropylamine, monoethanolamine, diethnolamine, triethanolamine, ethylenediamine and diethylenetriamine.

16. The process according to claim 15 wherein the compound of formula (I) is in an amount of 0.0001 to 5% by weight based on the weight of the lactonitrile.

17. The process according to claim 1 wherein the hydrogen cyanide is in an amount of 0.001 to 2% by weight based on the weight of the lactronitrile.

18. The process according to claim 2 wherein a weight ratio of lactronitrile to water in the hydrating reaction is 5:95 to 80:20 and the hydrating reaction is carried out at a temperature of 0 to 120° C.

19. The process according to claim wherein the weight ratio is 20:80 to 60:40 and the temperature is 10 to 90° C.

* * * * *